(12) United States Patent
Calhoun et al.

(10) Patent No.: US 11,034,946 B2
(45) Date of Patent: Jun. 15, 2021

(54) GLYCOSYLATION INDEPENDENT PROTEINS

(71) Applicant: Research Foundation of The City University of New York, New York, NY (US)

(72) Inventors: David H. Calhoun, New York, NY (US); Erin S. Stokes, New York, NY (US); M. Lane Gilchrist, New York, NY (US)

(73) Assignee: Research Foundation of The City University of New York, New York, NY (US)

( * ) Notice: Subject to any disclaimer, the term of this patent is extended or adjusted under 35 U.S.C. 154(b) by 100 days.

(21) Appl. No.: 16/153,371

(22) Filed: Oct. 5, 2018

(65) Prior Publication Data

US 2019/0106691 A1   Apr. 11, 2019

Related U.S. Application Data

(60) Provisional application No. 62/568,534, filed on Oct. 5, 2017.

(51) Int. Cl.
| | |
|---|---|
| C12N 9/24 | (2006.01) |
| C12N 9/40 | (2006.01) |
| A61K 38/47 | (2006.01) |
| A61K 38/00 | (2006.01) |

(52) U.S. Cl.
CPC ............ *C12N 9/2465* (2013.01); *A61K 38/47* (2013.01); *C12Y 302/01022* (2013.01); *A61K 38/00* (2013.01)

(58) Field of Classification Search
CPC ................................ C12N 9/24; C12N 9/2465
See application file for complete search history.

(56) References Cited

U.S. PATENT DOCUMENTS 5,179,023 A * 1/1993 Calhoun ................ C07K 16/40
435/235.1

OTHER PUBLICATIONS

Stokes. Sep. 2017. Mutagenesis of human alpha-galactosidase A for the treatment of Fabry Disease. On the World Wide Web at: academicworks.cuny.edu/gc_etds/2338/.*

* cited by examiner

*Primary Examiner* — Karen Cochrane Carlson
(74) *Attorney, Agent, or Firm* — Hoffman & Baron, LLP (57) ABSTRACT

A engineered alpha-galactosidase A polypeptide comprising SEQ ID NO: 1 having at least one non-glycosylation mutation; and at least one glycosylation compensatory mutation is claimed.

7 Claims, 3 Drawing Sheets
(3 of 3 Drawing Sheet(s) Filed in Color)
Specification includes a Sequence Listing.

```
      20   205  2    215        Human α-Gal A positions
       :    :   :     :
      M FY XS  S   L  X  SSD    Fabry patient mutations: (See legend for full list)
 198  IVYSCEWPLYMWPFQKPNYT 217  Active site: (EY: blue / highlight), residues for
      (SEQ ID NO: 4)             mutation (MWF: green/underline)
```

GLYCOSYLATION INDEPENDENT PROTEINS

CROSS-REFERENCE TO RELATED APPLICATION

The present application claims the benefit of U.S. Provisional Application Ser. No. 62/568,534 filed on Oct. 5, 2017, which is hereby incorporated by reference in its entirety.

BACKGROUND

Fabry disease (MIM: 301500) is caused by a deficiency of the lysosomal enzyme alpha-galactosidase A (α-Gal A) that leads to early death due to occlusive disease of the heart, kidney, and brain. Clinical trials of enzyme replacement therapy for Fabry disease patients revealed only limited therapeutic efficacy and the enzyme does not pass the blood-brain barrier. There are significant side effects and many patients develop antibodies even in clinical trials that involve a single infusion of enzyme. It is recognized that there is a need for improved therapies for this disease. Clinical trials indicate that the immune response is correlated with the dose of enzyme administered. For example, therapeutic doses of 1.0 and 0.2 mg/kg body weight of alpha-galactosidase A result in 88% and 21% of patients with IgG response.

Hence there exists a long standing need to provide a treatment regimen that requires lower doses of enzyme, thereby providing for more effective therapeutic effects and less frequent infusions. In particular, there is a need to provide an enzyme therapeutic that allow for targeted delivery within the body and are sufficiently biologically active upon intracellular uptake.

SUMMARY OF THE INVENTION

In one embodiment, the present invention provides an engineered alpha-galactosidase A polypeptide comprising SEQ ID NO: 1 having at least one non-glycosylation mutation; and at least one glycosylation compensatory mutation.

In one embodiment, the engineered alpha-galactosidase A polypeptide disclosed herein includes at least one of the following mutations: V137P, G138P, N139Q, K140P, T141P, A190P, L191P, N192Q, R193P, T194P, K213P, N215Q, Y216P, and T217P.

In one embodiment, the engineered alpha-galactosidase A polypeptide disclosed herein includes at least one of the following mutations: Y134 R/K/E/D, V137 R/K/E/D, Y184 R/K/E/D, S188 R/K/E/D, S197 R/K/E/D, V199R/K/E/D, S201 R/K/E/D, C202 R/K/E/D, W204 R/K/E/D, P205 R/K/E/D, Y207 R/K/E/D, M208 R/K/E/D, W209 X/R/K/E/D, P210 R/K/E/D, F211X Q212 R/K/E/D, P214 R/K/E/D, and Y216 R/K/E/D,; wherein X is any amino acid except the native residue.

In one embodiment, the present invention provides a method of treating occlusive disease of the brain comprising administering to a patient in need thereof an effective amount of the engineered alpha-galactosidase A polypeptide disclosed herein.

In one embodiment, the present invention provides a method of treating Fabry disease comprising administering to a patient in need thereof an effective amount of the engineered alpha-galactosidase A polypeptide disclosed herein.

BRIEF DESCRIPTION OF THE FIGURES

The patent or patent application contains at least one drawing executed in color. Copies of this patent or patent application publication with color drawing(s) will be provided by the U.S. Patent and Trademark Office upon request and payment of the necessary fee.

DETAILED DESCRIPTION

The present disclosure provides non-glycosylated derivatives of alpha-galactosidase A or glycosylation independent alpha-galactosidase A. The non-glycosylated derivatives of alpha-galactosidase A or glycosylation independent alpha-galactosidase A disclosed herein includes an engineered alpha-galactosidase A polypeptide having at least one non-glycosylation mutation; and at least one glycosylation compensatory mutation.

Figure 1:
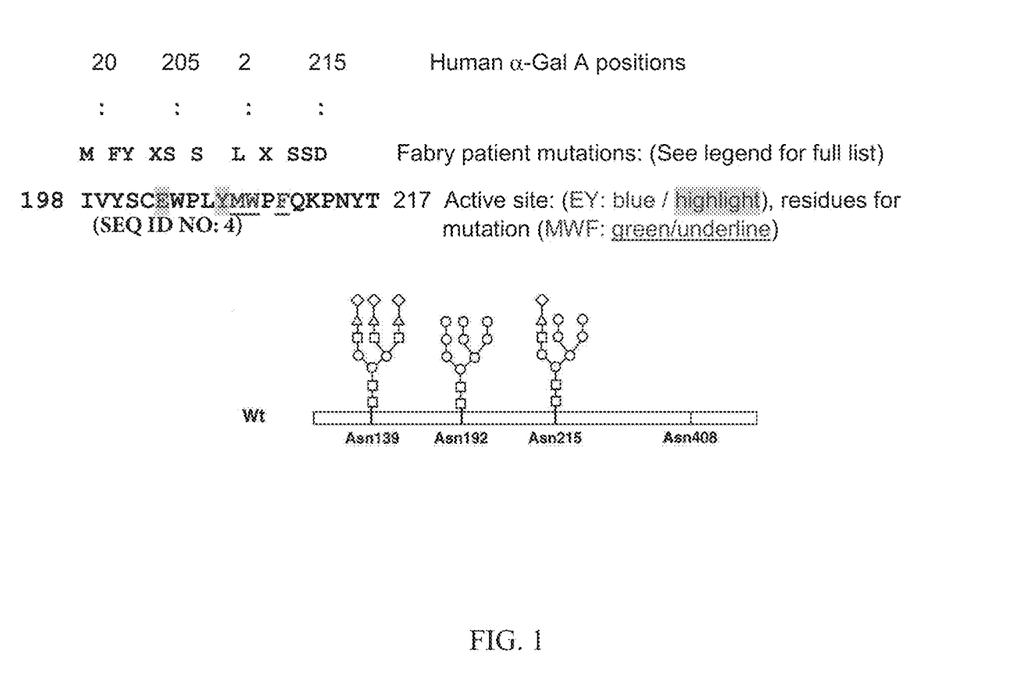
FIG. 1. Sites identified for mutation near glycosylation consensus NYT (215-217). Fabry patient mutations: V199M, S201F/Y, C202Y/W, W204X, P205S*/L/T/R, Y207S/C, P210L/S, Q212X, P214S, N215S*, Y216D/C (*late onset) (fabry-database.org/mutants/). Diagram (bottom) from [3].

There are four potential glycosylation sites, Asn139, Asn192 and Asn215, (Asn408 is not glycosylated) for human α-Gal A (FIG. 1) enzyme GenBank accession number AAP36507. Glycosylation at these three positions are required for full activity and solubility of the enzyme. Mutants lacking glycosylation sites 1 (N139), 2 (N192), or 3 (N215) retain 91.5%, 44.5%, and 3.9% of the wild type secreted activity, and double and triple mutants (sites 1-2, 1-3, 2-3, and 1-2-3) have undetectable (<1.4%) activity.

A non-glycosylation mutation is any mutation that causes loss of glycosylation at a natively glycosylated amino acid residue or site. The mutation may be a substitution mutation or deletion. A non-glycosylation mutation includes one or more mutations.

In one embodiment, substitution of the asparagine at N139, N192, or N215 with any amino acid other than asparagine will result in loss of glycosylation at positions 139, 192, or 215. Likewise, deletion of N139, N192, or N215 will result in loss of glycosylation. Furthermore, a substitution or deletion mutation that disrupts the N-glycosylation consensus sequence will result in loss of glycosylation. The N-glycosylation consensus being AsnXxxSer/Thr/Cys, where Xxx can be any amino acid except proline.

In one embodiment, one or more of the following mutations result in loss of glycosylation at N139: V137P, G138P, N139Q, K140P, and T141P.

In one embodiment, one or more of the following mutations result in loss of glycosylation at N192: A190P, L191P, N192Q, R193P, and T194P.

In one embodiment, one or more of the following mutations result in loss of glycosylation at N215: K213P, N215Q, Y216P, and T217P.

In one embodiment, the non-glycosylation mutation includes deletion of at least one of N139, N192, and N215.

The present disclosure provides compensatory mutations that restore functionality of the non-glycosylated alpha-galactosidase A enzyme described above. As used herein, a mutation that improves alpha-galactosidase A enzyme (having a non-glycosylation mutation) function is a glycosylation compensatory mutation.

It has been discovered that one or more mutations of amino acid residues at or near the normally glycosylated locations (N139, N192, and N215) to a polar or charged amino acid will restore functionality lost by non-glycosylation at one or more of N139, N192, and N215. Without wishing to be bound by theory, it is believed that glycosylation at positions N139, N192, and N215 interact with neighboring hydrophobic side chains, and loss of glycosylation results in protein misfolding, and solubility and aggregation issues. Hydrophobic amino acid residues are known in the art, and include Ala (A), Val (V), Ile (I), Leu (L), Met (M), Phe (F), Tyr (Y), and Trp (W). Therefore, substitution of neighboring hydrophobic residues with polar or uncharged amino acid residues will compensate for the loss of glycosylation.

The glycosylation compensatory mutation may be within 5, within 10, or within 20 amino acids from the normally glycosylated location, which is nonglycosylated.

Polar or charged amino acid residues are known in the art. Polar or charged amino acid residues include Ser (S), Thr (T), Cys (C), Tyr (Y), Gln (Q), Asp (D), Glu (E), Lys (K), Arg (R), and His (H).

In one embodiment, the present disclosure provides an engineered alpha-galactosidase A polypeptide having a non-glycosylation mutation at one or more of positions N139, N192 and N215; and compensatory mutation at one or more of positions: Y134, V137, Y184, S188, S197, V199, S201, C202, W204, P205, Y207, M208, W209, P210, F211, Q212, P214, Y216, and T217.

In another embodiment, the compensatory mutation includes substitution of the WT amino acid residue at Y134, V137, F145, Y184, S188, S197, V199, S201, C202, W204, P205, Y207, M208, W209, P210, F211, Q212, P214, Y216, T217 and Y222, with a polar or charged amino acid residue.

In another embodiment, the compensatory mutation is selected from the group consisting of: Y134R/K/E/D, V137R/K/E/D, Y184 R/K/E/D, S188 R/K/E/D, S197 R/K/E/D, V199R/K/E/D, S201R/K/E/D, C202R/K/E/D, W204R/K/E/D, P205R/K/E/D, Y207R/K/E/D, M208R/K/E/D, W209X/R/K/E/D, P210R/K/E/D, F211X Q212R/K/E/D, P214R/K/E/D, and Y216R/K/E/D,; wherein X is any amino acid except the native residue.

In one embodiment, the engineered alpha-galactosidase A polypeptide includes a non-glycosylation mutation selected from the group consisting of V137P, G138P, N139Q, K140P, and T141P. In this embodiment, the glycosylation compensatory mutation is selected from the group consisting of Y134 R/K/E/D, V137 R/K/E/D, and F145 R/K/E/D. Alternatively, in this embodiment, the glycosylation compensatory mutation is a deletion of one or more of Y134 and V137.

In one embodiment, the engineered alpha-galactosidase A polypeptide includes a non-glycosylation mutation is selected from the group consisting of A190P, L191P, N192Q, R193P, and T194P. In this embodiment, the glycosylation compensatory mutation is selected from the group consisting of Y184 R/K/E/D, S188 R/K/E/D, S197 R/K/E/D, and V199 R/K/E/D. Alternatively, in this embodiment, the compensatory mutation is a deletion selected from the group consisting of Y184, S188, S197, and V199.

In one embodiment, the engineered alpha-galactosidase A polypeptide includes a non-glycosylation mutation selected from the group consisting of K213P, N215Q, Y216P, and T217P. In this embodiment, the glycosylation compensatory mutation may be at least one of S197 R/K/E/D, V199 R/K/E/D, S201 R/K/E/D, C202 R/K/E/D, W204 R/K/E/D, P205 R/K/E/D, Y207 R/K/E/D, M208 R/K/E/D, W209 X/R/K/E/D, P210 R/K/E/D, F211X, Q212 R/K/E/D, P214 R/K/E/D, Y216 R/K/E/D, and Y222 R/K/E/D. Alternatively, in this embodiment, the compensatory mutation may be at least one deletion selected from the group consisting of S197, V199, S201, C202, W204, P205, Y207, M208, W209, P210, F211 Q212, P214, and Y216.

In one embodiment, the non glycosylation mutation is selected from the group consisting of K213P, N215Q, Y216P, and T217P; and the glycosylation compensatory mutation is a deletion or substitution of least one of M208, W209, P210 and F211.

In one embodiment, the non-glycosylation mutation is N215Q and the glycosylation compensatory mutation is at least one of M208E and F211X. In one embodiment, F211X is selected from the group consisting of F211H, F211R, F211K, F211E, and F211D.

Functional variants of the engineered polypeptides disclosed herein have been contemplated. As used herein, a functional variant includes a polypeptide having at least 99%, at least 95%, at least 90%, or at least 80% identity to SEQ ID NO: 1; wherein SEQ ID NO: 1 includes at least one non-glycosylation mutant, and at least one glycosylation compensatory mutation. Functional variants may be derived from non-human sources.

Functional fragments of the engineered polypeptides disclosed herein have been contemplated. As used herein, a functional fragment includes a polypeptide having between 400-428, 400-420, or 375-400 consecutive amino acids of SEQ ID NO: 1, wherein SEQ ID NO: 1 includes at least one non-glycosylation mutant and at least one glycosylation compensatory mutation.

In one embodiment, the present disclosure provides a polynucleotide that encodes for the engineered polypeptide disclosed herein. In one embodiment, the polynucleotide is in a vector.

Other mutations that aid in dimer stability increased catalysis have been contemplated. Such mutations are described in U.S. Provisional Application Nos. 62/207,856 and 62/207,849; and U.S. patent application Ser. No. 15/243,637, all of which are incorporated by reference in their entirety.

The present disclosure provides methods of treating Fabry disease by administering the engineered polypeptides disclosed herein to a patent in need thereof.

The engineered alpha-galactosidase polypeptide provides improved expression. The disclosed polypeptide may be expressed in systems without the need of glycosylation. Therefore, the polypeptides disclosed herein may be expressed in prokaryotes. In one embodiment, the present disclosure provides for expression of the engineered alpha-galactosidase polypeptide in *e. coli.*

The engineered alpha-galactosidase polypeptide disclosed herein provides improved ability to cross the blood brain barrier. In one embodiment, the engineered alpha-galactosidase polypeptide disclosed herein may be used to treat occlusive disease of the brain.

The engineered alpha-galactosidase polypeptide disclosed herein provides increased resistance to protease and therefore provides increased half-life in the patient to which it is administered.

The protein or polypeptide of the invention can be produced by conventional chemical methods, such as solid phase synthesis (using e.g. FMOC and BOC techniques), and solution phase synthesis. These proteins or polypeptides may also be produced in bacterial or insect cells or other eukaryotic transcriptional in vivo system, as detailed in the below-noted Current Protocols in Molecular Biology, Chapter 16. Following production, the protein or polypeptide are purified from the cells in which they have been produced. Polypeptide purification and isolation methods are known to the person of skill in the art and are detailed e.g., in Ausubel et al. (eds.) Current Protocols in Molecular Biology, Chapter 16, John Wiley and Sons, 2006 and in Coligan et al. (eds.). Current Protocols in Protein Science, Chapters 5 and 6, John Wiley and Sons, 2006. Advantageously, the protein or polypeptide may be produced as a fusion with a second protein, such as Glutathione-S-transferase (GST) or the like, or a sequence tag, such as the Histidine tag (His-tag) sequence. The use of fusion or tagged proteins simplifies the purification procedure, as detailed in the above-noted Current Protocols in Molecular Biology, Chapter 16, and in the instructions for His-tag protein expression and purification kits [available, e.g. from Qiagen GmbH, Germany].

As used herein, the term "purified" refers to a compound (e.g., alpha galctosidase A and derivatives disclosed herein) having been separated from a component of the composition in which it was originally present. The term purified can sometimes be used interchangeably with the term "isolated". Thus, for example, "purified or isolated quercetin" has been purified to a level not found in nature. A "substantially pure" compound or molecule is a compound or molecule that is lacking in most other components (e.g., 30, 40, 50, 60, 70, 75, 80, 85, 90, 95, 96, 97, 98, 99, 100% free of contaminants). By opposition, the term "crude" means compounds or molecules that have not been separated from the components of the original composition in which it was present. Therefore, the terms "separating", "purifying" or "isolating" refers to methods by which one or more components of the biological sample are removed from one or more other components of the sample. A separating or purifying step preferably removes at least about 70% (e.g., 70, 75, 80, 85, 90, 95, 96, 97, 98, 99, 100%), more preferably at least about 90% (e.g., 90, 91, 92, 93, 94, 95, 96, 97, 98, 99, 100%) and, even more preferably, at least about 95% (e.g., 95, 96, 97, 98, 99, 100%) of the other components present in the sample from the desired component. For the sake of brevity, the units (e.g., 66, 67 . . . 81, 82, . . . 91, 92% . . . ) have not systematically been recited but are considered, nevertheless, within the scope of the present invention.

In accordance with one embodiment, the delivery system and/or delivery vehicle can be provided in conjunction with a local drug delivery apparatus. A local drug delivery apparatus can be a medical device for implantation into a treatment site of a living organism and can include at least one delivery vehicle and/or a therapeutic agent in a therapeutic dosage releasably affixed to the medical device. A local delivery apparatus can include a material for preventing the delivery vehicle and/or the therapeutic agent from separating from the medical device prior to implantation of the medical device at the treatment site, the material being affixed to the medical device or a component of the delivery system.

A delivery vehicle and/or a therapeutic agent may be affixed to any number of medical devices. For example, the delivery vehicles and systems can be associated with or fixed with pumps, catheters, or implants. A delivery system may be affixed to minimize or substantially eliminate the biological organism's reaction to the introduction of the medical device utilized to treat a separate condition. For example, stents, catheters, implants, balloons, self-expandable or nor, degradable or not, can be utilized in conjunction with the delivery system.

The components of the delivery system can be administered in vivo by use of a pharmaceutically acceptable carrier in the form of a composition. By "pharmaceutically acceptable" is meant a material that is not biologically or otherwise undesirable, i.e., the material may be administered to a subject, along with the components of the delivery system, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of pharmaceutically-acceptable carriers include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the delivery system, which matrices are in the form of shaped articles, e.g., films. It will be apparent to those persons skilled in the art that certain carriers may be more preferable depending upon, for instance, the route of administration and concentration of composition being administered.

Pharmaceutical compositions for use in conjunction with the delivery system may include carriers, thickeners, diluents, buffers, preservatives, surface active agents and the like in addition to the delivery vehicle and/or the therapeutic agent. Pharmaceutical compositions may also include one or more active ingredients such as antimicrobial agents, anti-inflammatory agents, anesthetics, and the like.

A pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The delivery system can be administered intravenously, intraperitoneally, intramuscularly, subcutaneously, intracavity, or transdermally.

Parenteral administration, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Preparations for parenteral administration can include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral carriers include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like.

Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

The present invention is illustrated in further details by the following non-limiting examples.

EXAMPLES

In Situ Enzyme Assay for Colonies of *P. pastoris* Using the Artificial Substrate X-a-Gal.

In situ enzyme assays used nitrocellulose membranes (No. 21850, 0.45-mm pore size, VWR, Plainfield, N.J.)

visualized by a change in color from light yellow to blue 1 to 3 h after exposure to the substrate. This assay was adapted from Zhu, A., Monahan, C., Zhang, Z., Hurst, R., Leng, L., and Goldstein, J. (1995) High-level expression and purification of coffee bean a-galactosidase produced in the yeast *Pichia pastoris*. Arch. Biochem. Biophys. 324, 65-70.

A colorimetric patch test is used to test the ability of compensatory mutations to rescue non-glycosylation alpha-galactosidase A mutants.

Figure 2:
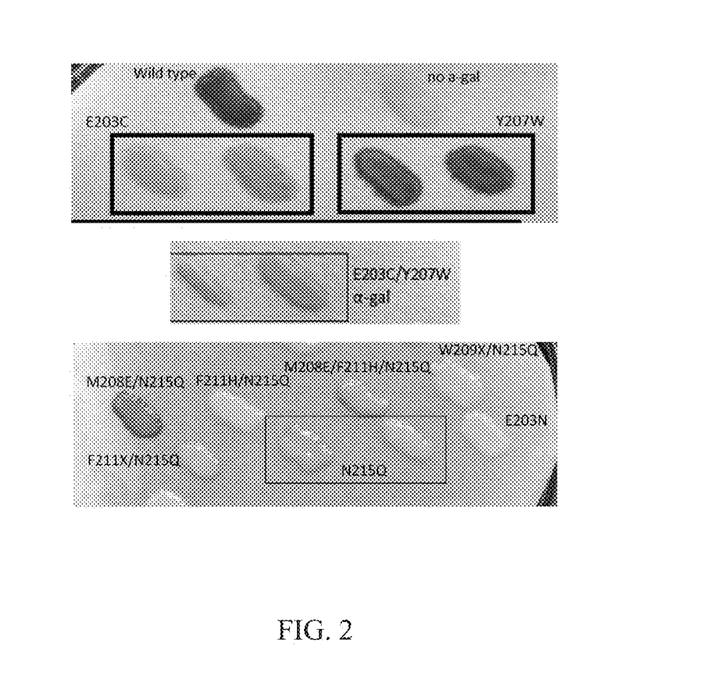
FIG. 2. Qualitative screen with 5-bromo-4-chloro-3-indolyl α-D-galactopyranoside (X-α-Gal), for α-Gal A activity in *P. pastoris* derivatives expressing enzymes with mutations in the active site (E203C, E203N, and Y207W) and in the 198-217 region (M208E, W209X, F211X, F211H, N215Q, alone and in combinations) (Stokes, unpublished).

Compensatory mutations were introduced (e.g., M208E) that stabilize the enzyme activity of a glycosylation negative (site 3) α-Gal A N215Q mutant (FIG. 2). The N215Q allele reduces α-Gal activity as predicted (FIG. 2: compare wild type with N215Q alone). This loss of activity is fully or partially reversed (FIG. 2) by the M208E allele, unaffected or stimulated by the F211X allele and by the combined M208E and F211H alleles, and further inhibited by the F211H and W209X alleles. These colorimetric patch tests are qualitative. Enzyme purification and complete kinetic analysis are carried out as previously described. Mutants lacking glycosylation sites 1 (N139Q) and 2 (N192Q) (FIG. 1) were reported to retain 91.5% (site 1) and 44.5% (site 2) of the wild type activity.

The glycosylation independent derivatives of the human α-Gal A disclosed herein are used for in vitro mutagenesis and directed evolution experiments in *Escherichia coli* and *Pichia pastoris* to further optimize enzyme activity and function.

```
-WT alpha-galactosidase A
                                                              SEQ ID NO: 1
MQLRNPELHL GCALALRFLA LVSWDIPGAR ALDNGLARTP TMGWLHWERF MCNLDCQEEP     60

DSCISEKLFM EMAELMVSEG WKDAGYEYLC IDDCWMAPQR DSEGRLQADP QRFPHOIRQL    120

ANYVHSKGLK LGIYADVG[N]K TCAGFPGSFG YYDIDAQTFA DWGVDLLKFD GCYCDSLENL  180

ADGYKHMSLA L[N]RTGRSIVY SCEWPLYMWP FQKP[N]YTEIR QYCNHWRNFA DIDDSWKSIK  240

SILDWTSFNQ ERIVDVAGPG GWNDPDMLVI ONFOLSWNQQ VTQMALWAIM AAPLFMSNDL    300

RHISPQAKAL LQDKDVIAIN QDPLGKQGYQ LRQGDNFEVW ERPLSGLAWA VAMINRQEIG    360

GPRSYTIAVA SLGKGVACNP ACFITQLLPV KRKLGFYEWT SRLRSHI[N]PT GTVLLQLENT  420

MQMSLKDLL

[BOLD] - glycosylation site: N215, N139, and N192.
GREEN - potential compensatory mutation sites for N215Q: S197, V199, S201,
C202, W204, P205, Y207, P210, Q212, P214, Y216, M208, W209, and F211X.
GREEN - potential compensatory mutation sites for N139Q and N192Q: Y134, and
V137; and Y184, S188, S197, and V199.
``` placed on YPDS petri plates with zeocin (100 mg/ml). Colonies that grew on selective media after electroporation were patched onto the membranes using sterile wooden toothpicks (Diamond Brands, Inc., Minneapolis, Minn.). The colonies were grown directly on the membrane overnight at 30° C. and then transferred to the surface of an MM plate for the enzyme induction by methanol. After incubation at 30° C. overnight, the membranes with colonies growing on top of them were placed on Whatman No. 4 filters (No. 1001 125, Whatman, Inc., Clifton, N.J.) saturated with the chromogenic substrate X-a-gal (No. 917591, Boehringer Mannheim, Indianapolis, Ind.) solution (1 mg/ml) in 40 mM sodium acetate, pH 4.5, and incubated at 37° C. Those colonies positive for a-galactosidase A activity were

Examples

Cell Strains and Plasmids.

The *P. pastoris* host strain X-33 (No. K1740-01), *E. coli* strains TOP10 (No. C4040-50) and TOP10F' (No. C665-11), plasmid pPICZαA (No. K1740-01), and TOPO® XL PCR cloning kit (No. K4700-10) were purchased from Invitrogen.

Bioreactor Expression of Recombinant αGal in *P. pastoris*.

High-cell-density fermentation was carried out as previously described (Chen 2000) with a modified growth medium utilizing non-precipitating sodium hexametaphosphate as a phosphate source (Zhang 2000) and modified for a 7 L Applikon bioreactor. Fermentation medium of 3.5 L (0.93 g/l $CaSO_4$, 18.2 g/l $K_2SO_4$, 14.9 g/l $MgSO_4 \cdot 7H_2O$, 9 g/l (NH4)2SO4, 40.0 g/l glycerol) was autoclaved at 121° C. for 20 min in the vessel. After cooling to room temperature, filter sterilized sodium hexametaphosphate (25 g/l of fermentation basal salt medium dissolved in 500 ml of deionized water) and 0.435% PTM1 trace elements (CuSO4.5 H2O 6.0 g, NaI 0.08 g, MgSO4.H2O 3.0 g, Na2MoO4.2 H2O 0.2 g, H3BO3 0.02 g, CoCl2 0.5 g, ZnCl2 20.0 g, FeSO4.7 H2O 65.0 g, biotin 0.2 g, 5.0 ml H2SO4 per liter) were added to complete the fermentation medium. The pH was adjusted to 6.0 using ammonium hydroxide (28%).

Four frozen MGY cultures of 4 ml each were used to inoculate four 100 ml MGY cultures in 1-liter baffled flasks and grown at 250 rpm and 30° C. until the OD600 reached 2 to 6. The cultivation was divided into three phases, the glycerol batch, glycerol-fed batch, and methanol-fed batch. The glycerol batch phase was initiated with 400 ml of inoculum shake-flask culture added to 4 L of the fermentation medium containing 4% glycerol and an initial value of 100% dissolved oxygen until a spike was observed indicating complete consumption of glycerol. Next, the glycerol-fed batch phase was initiated and a 50% w/v glycerol feed rate of 18.15 ml/h/liter initial fermentation volume and maintained until a cell yield of 180 to 220 g/liter wet cells was achieved. At this point the glycerol feed was terminated manually and a methanol-fed batch phase was initiated by starting a 100% methanol feed containing 12 ml PTM1 trace salts per liter. Methanol was initially fed at 3.6 ml/h/liter of initial fermentation volume, then increased to 7.3 ml/h/liter and finally increased to 10.9 ml/h/liter of initial fermentation volume for the remainder of the fermentation. Dissolved oxygen spikes were used during the glycerol-fed batch phase and methanol-fed batch phase and to monitor substrate levels. A dissolved oxygen level of 40%, pH of 6, and temperature of 25° C. were maintained by an ADI 1030 regulator. Sampling was performed at the end of each phase and at lease twice daily and analyzed for cell wet weight and increased αGal activity over time. Cultivation was terminated once a plateau in αGal activity was observed.

Purification of αGal Using Double Affinity Chromatography.

Purification was as described (Chen 2000, Yasuda 2004) with minor modifications (below). Bioreactor supernatant was passed through a 0.2 µm hollow fiber filter (Spectrum Labs, No. M22M-300-01N) and subjected to diafiltration using a 50 kDa pore size hollow fiber filter (Spectrum Labs, No. M25S-300-01N) against wash buffer (0.1 M sodium acetate buffer, pH 6.0, 0.1 M NaCl, 1 mM MgCl2, 1 mM CaCl2, 1 mM MnCl2). The resulting supernatant was applied to a Con A Sepharose 4B (GE Healthcare No. 17-0440-01) column, pre-equilibrated with wash buffer, and washed with 5 column volumes of wash buffer. It was observed that near-saturating sugar eluent concentrations do not improve glycoprotein recovery as compared to lower concentrations and that elution phase pauses improve recovery. In accordance with these findings, elution of αGal was carried out using modified elution buffer I (0.5 M methyl-α-d-mannopyranoside, 0.25 M methyl-α-d-glucopyranoside in wash buffer) over 1.5 column volume blocks separated by 12-hour interval soaks. Elution was discontinued when the absorbance at 280 nm and enzyme assays showed negligible presence of protein and αGal activity. No substantial difference in recovered enzyme was observed between purifications carried out with modified elution buffer I versus sugar saturated elution buffer I (data not shown). The Con A pool was subjected to diafiltration using a 50 kDa pore size hollow fiber filter (Spectrum Labs, No. M25S-300-01N) against binding buffer (25 mM citrate-phosphate buffer, pH 4.8 containing 0.1 M NaCl).

The Con A pool was applied to an immobilized-d-galactose gel column (Thio-Gal, Pierce No. 20372) pre-equilibrated with binding buffer. The column was washed with 5 column volumes of binding buffer and αGal was eluted with elution buffer II (25 mM citrate-phosphate buffer, pH 5.5, 0.1 M NaCl, 0.1 M d-galactose) over 1.5 column volume blocks separated by 12 hour soaks. Fractions were assayed for enzyme activity and protein concentration and a peak tube with high specific activity was chosen as the sample to be used in a substrate saturation curve.

The purification protocol is modified for the purification of the Y207W mutant of alpha-galactosidase A. For this mutant, DEAE (Diethylaminoethyl) and SP (sulphopropyl, strong cation exchange) affinity media are used for purification. See FIG. 6.

Electrophoresis Analysis

Samples (8 µg) were mixed with an equal volume of reducing sample buffer (Bio-Rad Laemmli sample buffer with 5% β-mercaptoethanol) and heated for 5 minutes at 95° C. before loading on a Mini-Protean TGX Precast Gel 4-20% (w/v) (Bio-Rad No. 456-1094). Bands were visualized by Coomassie blue staining via the modified Fairbanks protocol.

Western Blot Analysis

Western blot analysis was performed using an anti-αGal polyclonal antibody produced in chicken (Pierce/ThermoSci #PA1-9528) and horseradish peroxidase-conjugated anti-Chicken IgY antibody (Sigma #A9046). After SDS-PAGE (2 µg of samples loaded), the gel was incubated with a nitrocellulose membrane (Whatman, No. 10402594) for 15 minutes at room temperature in Transfer Buffer (48 mM Tris, 39 mM glycine, 20% MeOH, pH 9.2) and the proteins were then transferred to the nitrocellulose membrane using a Bio-Rad Trans Blot SD Semi-Dry Transfer Cell. The membrane was blocked with 8% (w/v) non-fat dried milk in PBST [10 mM Na2HPO4, 1.8 mM KH2PO4, 137 mM NaCl, 2.7 mM KCl and 0.2% Tween 20 (pH 7.4)] at room temperature for 20 minutes. The membrane was then treated with primary antibody diluted in a milk/blot solution [1% (w/v) non-fat dried PBST] for 2 h at room temperature with mild shaking. After rinsing with PBST solution, the membrane was treated for 1 h at room temperature with secondary antibody diluted in the milk/blot solution. Protein bands were visualized on Kodak BioMax XAR film (VWR #1B1651454) with a Konica SRX-101A processor.

Enzyme and Protein Assays

Activity of αGal was assayed using the synthetic substrate, 4-methylumbelliferyl-α-d-galactopyranoside (MUG) as described (Chen 2000) with modifications to a microtiter plate format (below). Enzyme activity is measured in units/ml where one unit is defined as the amount of enzyme required to convert 1 nmole of MUG to 4-methylumbelliferone in one hour at 37° C. An aliquot of 3 µl was added to 27 µl of enzyme assay buffer (5 mM MUG in 40 mM sodium acetate buffer, pH 4.5). This mixture was incubated at 37° C. and 10 µl aliquots were taken at two time points and added to 290 µl of 0.1 M diethylamine in a microtiter plate to stop the reaction. Typically time points were chosen as 1-4 minutes and values that were proportional to time were considered valid. The fluorescence of each sample was measured at an excitation wavelength of 365 nm and an emission wavelength of 450 nm using a Tecan Infinite F200 microtiter plate reader. A standard curve of 10 µl of 0-0.5 nmol 4-methylumbelliferone dissolved in MeOH in 290 µl of 0.1 M diethylamine was used to quantitate MUG cleavage at specific time intervals. Analysis of the effects of MeOH indicated no effect on the 4-methylumbelliferone standard curve.

For samples containing higher protein concentrations, the BioRad DC Protein Assay (No. 500-0116) with a standard curve of (0.2-1.5) mg/ml was used according to the manufacturer's specifications. For dilute samples of purified αGal, a more sensitive fluorescence-based fluorescamine assay with a standard curve containing lower protein concentrations of (4.0-160) µg/ml was used. Briefly, 150 µl of 0.05 M sodium phosphate buffer and 50 µl of 1.08 mM fluorescamine dissolved in acetone were added to an aliquot of 50 µl of the sample and standards, mixed and incubated for 12 minutes. The fluorescence of each sample was measured at an excitation wavelength of 400 nm and an emission wavelength of 460 nm. Bovine serum albumin (Bio-Rad No. 500-0112) was used as the standard in both assays. Absorbance and fluorescence measurements were conducted on a Tecan Infinite F200 microplate reader using 96-well plates.

Mass Spectrometry of a Purified Mutant Enzyme

Mass spectrometry is used to analyze the mutant enzyme. SDS-PAGE gel slices are washed, de-stained, reduced using 10 mM dithiothreitol, alkylated using 100 mM iodoacetamide, and digested using trypsin. Peptides are then extracted from the gel two times, dried, and re-suspended in a 5% acetonitrile and 2% formic acid mixture. One third of each sample is loaded onto a C18 PepMap1000 microprecolumn (300 µm I.D., 5 mm length, 5 µm beads, Thermo Scientific) at a flow-rate of 5 µl/min, and subsequently onto an analytical C18 column (75 µm I.D., 3 µm beads, Nikkyo Technos Co.) at a flow rate of 300 nl/min. The gradient was 40 min long in the range 5 to 45% B (buffer A was 0.1% formic acid in water, and buffer B was 0.1% formic acid in acetonitrile). Eluted peptides are applied by electrospray directly into the LTQ-Orbitrap XL mass spectrometer from Thermo Scientific, operating in a 300 to 1800 m/z mass range. Tandem mass spectrometry was performed by collision induced dissociation using nitrogen as a collision gas. The resulting spectra were analyzed using Mascot and Proteome Discoverer 1.3 (Thermo Scientific) to identify the peptides in the sample.

Thermostability and pH Optimum of WT and Mutant αGal

Purified enzyme samples are diluted in 25 mM citrate-phosphate buffer, pH 5.5, 0.1 M NaCl, 0.01 M D-galactose. Samples of 50 µl were incubated in triplicate at 50° C., 30° C., and 40° C. Aliquots of 3 µl are removed for enzyme assays every 15 minutes for two hours. Samples are assayed in 0.02 M citrate buffer, pH 3.0-pH 6.5, containing 2 mM MUG.

Characterization of Kinetic Properties

Substrate saturation curves for αGal have been reported using MUG at concentrations up to 2 mM, 5 mM, and 10 mM (in the presence of 0.1% BSA and 0.67% EtOH). We noted that under our experimental conditions MUG is fully soluble at 2 mM, partially soluble at 5 mM, and chemically oversaturated at higher concentrations. Other investigators reported the use of sonication or detergent treatment to increase the solubility of MUG, but we avoided this approach in order to avoid potential artifacts due to the use of these techniques. Substrate saturation curves using 2 mM and 5 mM MUG as the highest concentrations were carried out and the kinetic parameters for αGal were calculated separately obtaining similar values. The values reported here were obtained using a substrate saturation curve of 0.3 to 2 mM MUG since this is the highest concentration that is fully soluble under our experimental conditions. The Km and Vmax values were calculated using Lineweaver-Burk and non-linear regression through the program Sigma-Plot (Systat Software, San Jose, Calif.).

Kinetic parameters were also determined using the colorimetric substrate, para-nitrophenyl-α-d-galactopyranoside (PNPaGal) [70]. Purified enzymes were diluted to approximately 20,000 units/mL as determined by fluorescent MUG assay. These diluted samples were then added at a proportion of 1:9 citrate-phosphate buffer (0.1 M) containing 7-50 mM PNPαGal. Aliquots of 20 µl of the enzymatic reaction were removed at 15 minute intervals to terminate the reaction over the course of an hour and added to 320 µl of borate buffer (pH 9.8) in a microplate [71]. Product formation was monitored by absorbance at 400 nm. Linear reaction velocities were observed for all measurements. A standard curve of 0-150 µM p-nitrophenylate in borate buffer (pH 9.8) [71] was used to quantitate product formation. Km and Vmax parameters were determined through non-linear regression using Sigma-Plot (Systat Software, San Jose, Calif.).

Protein Structure Analysis

The crystal structure of αGal (PDB 1R47) was viewed and analyzed in PyMOL (Delano Scientific). The MSLDKLL and QMSLKDLL peptides corresponding to the last 7 or 8 C-terminal amino acids of αGal were built in PyRosetta [72] and visualized in PyMOL [73]. Interatomic distances were measured using the PyMOL wizard distance command.

A homology model of the coffee bean α-galactosidase was generated on the Phyre2 server. The primary sequence of coffee bean α-galactosidase (GenBank No. AAA33022.1) was set as the query. The crystal structure of rice α-galactosidase (73% sequence identity to coffee α-galactosidase, PDB#1UAS) was set as the template. Superposition of the coffee homolog and human crystal structure of αGal (PDB#1R47) was conducted in PyMOL. Primary sequence alignments were carried out in ClustalOmega (EMBL-EBI).

In Situ Enzyme Assay.

In situ enzyme assay for colonies of P. pastoris using the artificial substrate X-a-Gal. In situ enzyme assays (12) used nitrocellulose membranes (No. 21850, 0.45-mm pore size, VWR, Plainfield, N.J.) placed on YPDS petri plates with zeocin (100 mg/ml). Colonies that grew on selective media after electroporation were patched onto the membranes using sterile wooden toothpicks (Diamond Brands, Inc., Minneapolis, Minn.). The colonies were grown directly on the membrane overnight at 30° C. and then transferred to the surface of an MM plate for the enzyme induction by methanol. After incubation at 30° C. overnight, the membranes with colonies growing on top of them were placed on Whatman No. 4 filters (No. 1001 125, Whatman, Inc., Clifton, N.J.) saturated with the chromogenic substrate X-a-gal (No. 917591, Boehringer Mannheim, Indianapolis, Ind.) solution (1 mg/ml) in 40 mM sodium acetate, pH 4.5, and incubated at 37° C. Those colonies positive for a-galactosidase A activity were visualized by a change in color from light yellow to blue 1 to 3 h after exposure to the substrate. This assay was adapted from Zhu, A., Monahan, C., Zhang, Z., Hurst, R., Leng, L., and Goldstein, J. (1995) High-level expression and purification of coffee bean a-galactosidase produced in the yeast Pichia pastoris. Arch. Biochem. Biophys. 324, 65-70.

Example 1: In Situ Enzyme Assay Engineered Alpha-Galactosidase

A polypeptide having different combinations of E203C, Y207W, E203N, M208E, W209X, F211X, F211H, and N215Q mutations.

The in situ enzyme assay described above was used to test the following engineered alpha-galactosidase A polypeptides: WT; and combinations of E203C, Y207W, E203N, M208E, W209X, F211X, F211H, and N215Q. See FIG. 2.

Example 2: Kinetic Characterization of WT Alpha-Galactosidase A Polypeptide

WT alpha-galactosidase A polypeptide was expressed and purified by the methods described above.

Characterization of kinetic properties where determined as described above. Table 1 provides the various kinetic parameters. See below for the 0Lineweaver-Burke plot showing the same.

TABLE 1

| Km (mM) | Vmax (mmol/hr/mg) | kcat (1/s) | kcat/Km (1/sM) | Relative kcat/Km to WT |
|---|---|---|---|---|
| 0.66 ± 0.07 | 0.028 ± 0.0014 | 0.69 ± 0.04 | 1,056 ± 83 | 1 |

Example 3. Isolation and Kinetic Characterization of Stabilized Alpha-Galactosidase a Polypeptide Dimers Alpha-galactosidase A polypeptides having the Y207W mutation and W277C mutation are expressed and purified by methods described above.

Figure 3:
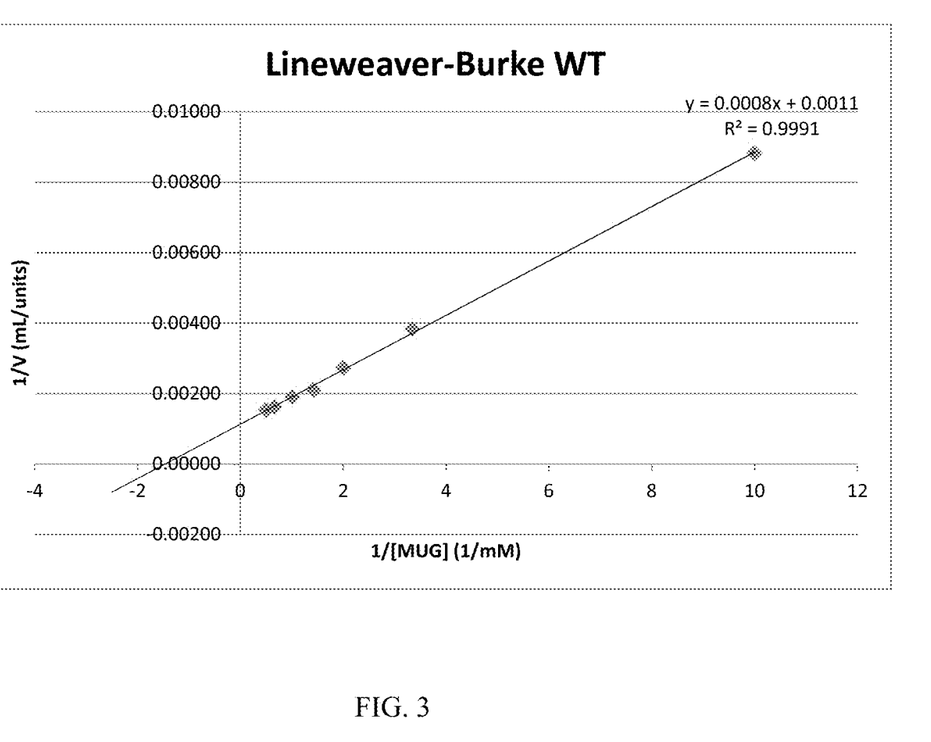
FIG. 3. Lineweaver-Burke WT

See FIG. 3 for the Lineweaver-Burke WT.

Example 4: Kinetic Characterization of Engineered Alpha-Galactosidase a Polypeptide Having the M208E/N215Q Mutation Engineered alpha-galactosidase A polypeptide having the M208E/N215Q mutation was expressed and purified by the methods described above.

Characterization of kinetic properties where determined as described above. Table 2 provides the various kinetic parameters. See below for the Lineweaver-Burke plot showing the same.

TABLE 2

| MUTATION | Km (mM) | Vmax (mmol/hr/mg) | kcat (1/s) | kcat/Km (1/sM) | Relative kcat/Km to WT |
|---|---|---|---|---|---|
| M208E/N215Q | 0.33 ± 0.0 | 0.091 ± 0.0 | 2.29 ± 0.0 | 6,860 ± 0 | 6.496 |

Figure 4:
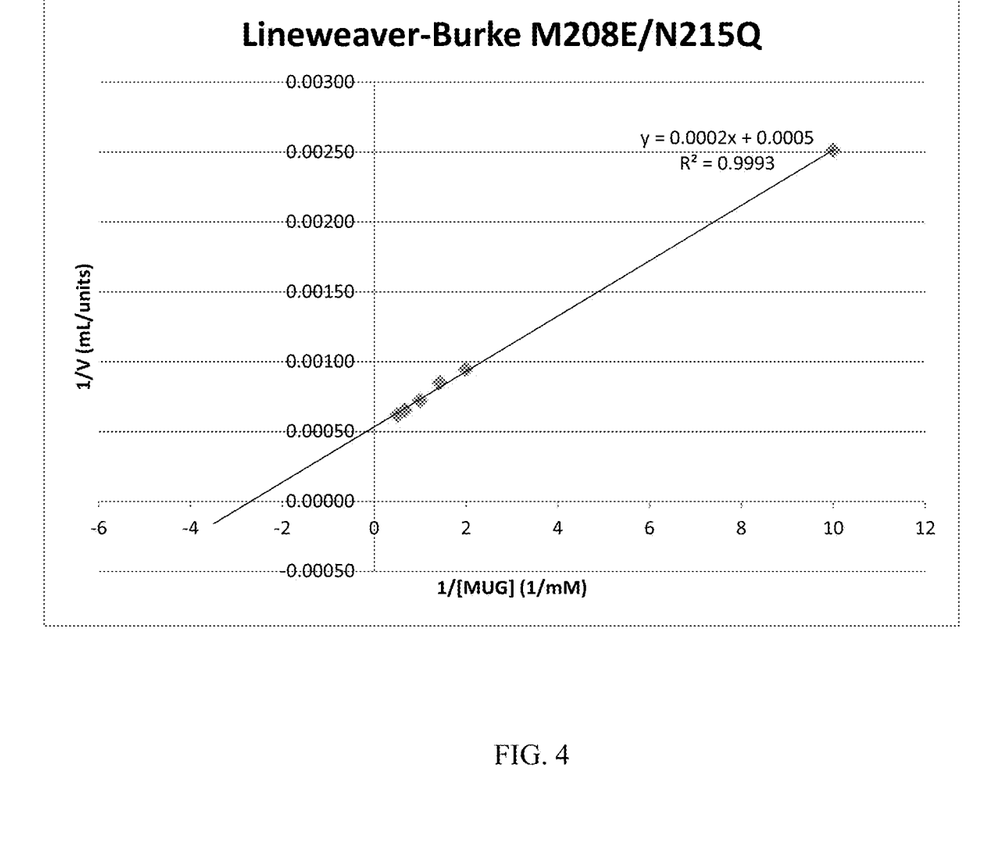
FIG. 4. Lineweaver-Burke M208E/N215Q

See FIG. 4 for the Lineweaver-Burke M208E/N215Q.

```
SEQUENCE LISTING

SEQ ID NO. 1 - WT alpha-galactosidase A (NP_000160)
MQLRNPELHL GCALALRFLA LVSWDIPGAR ALDNGLARTP TMGWLHWERF MCNLDCQEEP    60

DSCISEKLFM EMAELMVSEG WKDAGYEYLC IDDCWMAPQR DSEGRLQADP QRFPHGIRQL   120

ANYVHSKGLK LGIYADVGNK TCAGFPGSFG YYDIDAQTFA DWGVDLLKFD GCYCDSLENL   180

ADGYKHMSLA LNRTGRSIVY SCEWPLYMWP FQKPNYTEIR QYCNHWRNFA DIDDSWKSIK   240

SILDWTSFNQ ERIVDVAGPG GWNDPDMLVI GNFGLSWNQQ VTQMALWAIM AAPLFMSNDL   300

RHISPQAKAL LQDKDVIAIN QDPLGKQGYQ LRQGDNFEVW ERPLSGLAWA VAMINRQEIG   360

GPRSYTIAVA SLGKGVACNP ACFITQLLPV KRKLGFYEWT SRLRSHINPT GTVLLQLENT   420

MQMSLKDLL

SEQ ID NO. 2 - polynucleotide sequence encoding for alpha-galactosidase A.
atgcagctga
ggaacccaga actacatctg ggctgcgcgc ttgcgcttcg cttcctggcc ctcgtttcct
gggacatccc tggggctaga gcactggaca atggattggc aaggacgcct accatgggct
ggctgcactg ggagcgcttc atgtgcaacc ttgactgcca ggaagagcca gattcctgca
tcagtgagaa gctcttcatg gagatgcag agctcatggt ctcagaaggc tggaaggatg
caggttatga gtacctctgc attgatgact gttggatggc tcccaaaga gattcagaag
gcagacttca ggcagaccct cagcgctttc ctcatgggat tcgccagcta gctaattatg
ttcacagcaa aggactgaag ctagggattt atgcagatgt tggaaataaa acctgcgcag
gcttccctgg gagttttgga tactacgaca ttgatgccca gacctttgct gactgggggag
tagatctgct aaaatttgat ggttgttact gtgacagttt ggaaaatttg gcagatggtt
ataagcacat gtccttggcc ctgaatagga ctggcagaag cattgtgtac tcctgtgagt
ggcctcttta tatgtggccc tttcaaaagc ccaattatac agaaatccga cagtactgca
atcactggcg aaattttgct gacattgatg attcctggaa aagtataaag agtatcttgg
actggacatc ttttaaccag gagagaattt tgatgttgc tggaccaggg ggttggaatg
acccagatat gttagtgatt ggcaactttg gcctcagctg gaatcagcaa gtaactcaga
tggccctctg ggctatcatg gctgctcctt tattcatgtc taatgacctc cgacacatca
gccctcaagc caaagctctc cttcaggata aggacgtaat tgccatcaat caggaccct
tgggcaagca agggtaccag cttagacagg gagacaactt tgaagtgtgg aacgacctc
tctcaggctt agcctgggct gtagctatga taaaccggca ggagattggt ggacctcgct
```

SEQUENCE LISTING

```
cttataccat cgcagttgct tccctgggta aaggagtggc ctgtaatcct gcctgcttca
tcacacagct cctccctgtg aaaggaagc tagggttcta tgaatggact tcaaggttaa
gaagtcacat aaatcccaca ggcactgttt tgcttcagct agaaaataca atgcagatgt
cattaaaaga cttactttaa SEQ ID NO. 3 - WT alpha-galactosidase A (NM_000169.2)
   1    aaacaataac gtcattattt aataagtcat cggtgattgg tccgcccctg aggttaatct 61    taaaagccca ggttacccgc ggaaatttat gctgtccggt caccgtgaca atgcagctga 121    ggaacccaga actacatctg ggctgcgcgc ttgcgcttcg cttcctggcc ctcgtttcct 181    gggacatccc tggggctaga gcactggaca atggattggc aaggacgcct accatgggct 241    ggctgcactg ggagcgcttc atgtgcaacc ttgactgcca ggaagagcca gattcctgca 301    tcagtgagaa gctcttcatg gagatggcag agctcatggt ctcagaaggc tggaaggatg 361    caggttatga gtacctctgc attgatgact gttggatggc tccccaaaga gattcagaag 421    gcagacttca ggcagaccct cagcgctttc ctcatgggat tcgccagcta gctaattatg 481    ttcacagcaa aggactgaag ctagggattt atgcagatgt tggaaataaa acctgcgcag 541    gcttccctgg gagttttgga tactacgaca ttgatgccca gacctttgct gactgggggag 601    tagatctgct aaaatttgat ggttgttact gtgacagttt ggaaaatttg gcagatggtt 661    ataagcacat gtccttggcc ctgaatagga ctggcagaag cattgtgtac tcctgtgagt 721    ggcctcttta tatgtggccc tttcaaaagc ccaattatac agaaatccga cagtactgca 781    atcactggcg aaattttgct gacattgatg attcctggaa aagtataaag agtatcttgg 841    actggacatc ttttaaccag gagagaattg ttgatgttgc tggaccaggg ggttggaatg 901    acccagatat gttagtgatt ggcaactttg gcctcagctg gaatcagcaa gtaactcaga 961    tggccctctg ggctatcatg gctgctcctt tattcatgtc taatgacctc cgacacatca 1021    gccctcaagc caaagctctc ttcaggata aggacgtaat tgccatcaat caggaccct 1081    tgggcaagca agggtaccag cttagacagg gagacaactt tgaagtgtgg gaacgacctc 1141    tctcaggctt agcctgggct gtagctatga taaaccggca ggagattggt ggacctcgct 1201    cttataccat cgcagttgct tccctgggta aaggagtggc ctgtaatcct gcctgcttca 1261    tcacacagct cctccctgtg aaaggaagc tagggttcta tgaatggact tcaaggttaa 1321    gaagtcacat aaatcccaca ggcactgttt tgcttcagct agaaaataca atgcagatgt 1381    cattaaaaga cttactttaa aatgtttatt ttattgcc
```

While there have been described what are presently believed to be the preferred embodiments of the present invention, those skilled in the art will realize that other and further changes and modifications may be made thereto without departing from the spirit of the invention, and it is intended to claim all such modifications and changes as come within the true scope of the invention.

INCORPORATION OF SEQUENCE LISTING

Incorporated herein by reference in its entirety is the Sequence Listing for the above-identified Application. The Sequence Listing is disclosed on a computer-readable ASCII text file titled "Sequence_Listing_1038-158.txt", created on Oct. 5, 2018. The sequence.txt file is 7.5 KB in size.

The invention claimed is:

1. An engineered alpha-galactosidase A polypeptide having at least 90% identity to SEQ ID NO: 1 and having at least one non-glycosylation mutation and at least one glycosylation compensatory mutation, wherein said non-glycosylation mutation is N215Q; and wherein the glycosylation compensatory mutation is selected from the group comprising M208E, W209X and F211X, wherein X is any amino acid residue except the native residue.

2. An engineered alpha-galactosidase A polypeptide comprising SEQ ID NO: 1 having at least one non-glycosylation mutation; and at least one glycosylation compensatory mutation, wherein said non-glycosylation mutation is N215Q; and the glycosylation compensatory mutation is selected from the group consisting of g M208E, W209X and F211X, wherein X is any amino acid residue except the native residue.

3. The engineered alpha-galactosidase A polypeptide according to claim 2, wherein W209X is selected from the group consisting of W209D, W209E, W209K and W209R.

4. The engineered alpha-galactosidase A polypeptide according to claim 2, wherein F211X is selected from the group consisting of F211H, F211R, F211K, F211E, and F211D.

5. An engineered polynucleotide sequence, said sequence encoding for a polypeptide according to claim 2.

6. A method of treating occlusive disease of the brain comprising administering to a patient in need thereof an effective amount of the engineered alpha-galactosidase A polypeptide according to claim 2.

7. A method of treating Fabry disease comprising administering to a patient in need thereof an effective amount of the engineered alpha-galactosidase A polypeptide according to claim 2.

* * * * *

SEQUENCE LISTING

```
<160> NUMBER OF SEQ ID NOS: 4

<210> SEQ ID NO 1
<211> LENGTH: 429
<212> TYPE: PRT
<213> ORGANISM: Homo sapiens

<400> SEQUENCE: 1
```

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
                20                  25                  30

Asp Asn Gly Leu Ala Arg Thr Pro Thr Met Gly Trp Leu His Trp Glu
            35                  40                  45

Arg Phe Met Cys Asn Leu Asp Cys Gln Glu Glu Pro Asp Ser Cys Ile
        50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
```

420        425

<210> SEQ ID NO 2
<211> LENGTH: 1290
<212> TYPE: DNA
<213> ORGANISM: Homo sapiens

<400> SEQUENCE: 2

| | | | | | |
|---|---|---|---|---|---|
| atgcagctga | ggaacccaga | actacatctg | ggctgcgcgc | ttgcgcttcg | cttcctggcc | 60 |
| ctcgtttcct | gggacatccc | tggggctaga | gcactggaca | atggattggc | aaggacgcct | 120 |
| accatgggct | ggctgcactg | ggagcgcttc | atgtgcaacc | ttgactgcca | ggaagagcca | 180 |
| gattcctgca | tcagtgagaa | gctcttcatg | agatggcag | agctcatggt | ctcagaaggc | 240 |
| tggaaggatg | caggttatga | gtacctctgc | attgatgact | gttggatggc | tccccaaaga | 300 |
| gattcagaag | gcagacttca | ggcagaccct | cagcgctttc | ctcatgggat | tcgccagcta | 360 |
| gctaattatg | ttcacagcaa | aggactgaag | ctagggattt | atgcagatgt | tggaaataaa | 420 |
| acctgcgcag | gcttccctgg | gagttttgga | tactacgaca | ttgatgccca | gacctttgct | 480 |
| gactggggag | tagatctgct | aaaatttgat | ggttgttact | gtgacagttt | ggaaatttg | 540 |
| gcagatggtt | ataagcacat | gtccttggcc | ctgaatagga | ctggcagaag | cattgtgtac | 600 |
| tcctgtgagt | ggcctctta | tatgtggccc | tttcaaaagc | ccaattatac | agaaatccga | 660 |
| cagtactgca | atcactggcg | aaattttgct | gacattgatg | attcctggaa | agtataaag | 720 |
| agtatcttgg | actggacatc | ttttaaccag | agagaattg | ttgatgttgc | tggaccaggg | 780 |
| ggttggaatg | acccagatat | gttagtgatt | ggcaactttg | gcctcagctg | gaatcagcaa | 840 |
| gtaactcaga | tggccctctg | ggctatcatg | gctgctcctt | tattcatgtc | taatgacctc | 900 |
| cgacacatca | gccctcaagc | caaagctctc | cttcaggata | aggacgtaat | tgccatcaat | 960 |
| caggacccct | tgggcaagca | agggtaccag | cttagacagg | gagacaactt | tgaagtgtgg | 1020 |
| gaacgacctc | tctcaggctt | agcctgggct | gtagctatga | taaaccggca | ggagattggt | 1080 |
| ggacctcgct | cttataccat | cgcagttgct | tccctgggta | aaggagtggc | ctgtaatcct | 1140 |
| gcctgcttca | tcacacagct | cctccctgtg | aaaaggaagc | tagggttcta | tgaatggact | 1200 |
| tcaaggttaa | gaagtcacat | aaatcccaca | ggcactgttt | tgcttcagct | agaaaataca | 1260 |
| atgcagatgt | cattaaaaga | cttactttaa | | | | 1290 |

<210> SEQ ID NO 3
<211> LENGTH: 1418
<212> TYPE: DNA
<213> ORGANISM: Homo sapiens

<400> SEQUENCE: 3

| | | | | | |
|---|---|---|---|---|---|
| aaacaataac | gtcattattt | aataagtcat | cggtgattgg | tccgcccctg | aggttaatct | 60 |
| taaaagccca | ggttacccgc | ggaaatttat | gctgtccggt | caccgtgaca | atgcagctga | 120 |
| ggaacccaga | actacatctg | ggctgcgcgc | ttgcgcttcg | cttcctggcc | ctcgtttcct | 180 |
| gggacatccc | tggggctaga | gcactggaca | atggattggc | aaggacgcct | accatgggct | 240 |
| ggctgcactg | ggagcgcttc | atgtgcaacc | ttgactgcca | ggaagagcca | gattcctgca | 300 |
| tcagtgagaa | gctcttcatg | agatggcag | agctcatggt | ctcagaaggc | tggaaggatg | 360 |
| caggttatga | gtacctctgc | attgatgact | gttggatggc | tccccaaaga | gattcagaag | 420 |
| gcagacttca | ggcagaccct | cagcgctttc | ctcatgggat | tcgccagcta | gctaattatg | 480 |
| ttcacagcaa | aggactgaag | ctagggattt | atgcagatgt | tggaaataaa | acctgcgcag | 540 |

```
gcttccctgg gagttttgga tactacgaca ttgatgccca gacctttgct gactggggag    600
tagatctgct aaaatttgat ggttgttact gtgacagttt ggaaaatttg gcagatggtt    660
ataagcacat gtccttggcc ctgaatagga ctggcagaag cattgtgtac tcctgtgagt    720
ggcctcttta tatgtggccc tttcaaaagc ccaattatac agaaatccga cagtactgca    780
atcactggcg aaattttgct gacattgatg attcctggaa aagtataaag agtatcttgg    840
actggacatc ttttaaccag gagagaattg ttgatgttgc tggaccaggg ggttggaatg    900
acccagatat gttagtgatt ggcaactttg gcctcagctg aatcagcaa gtaactcaga     960 tggccctctg ggctatcatg gctgctcctt tattcatgtc taatgacctc cgacacatca   1020
gccctcaagc caaagctctc cttcaggata aggacgtaat tgccatcaat caggacccct   1080
tgggcaagca agggtaccag cttagacagg gagacaactt tgaagtgtgg gaacgacctc   1140
tctcaggctt agcctgggct gtagctatga taaaccggca ggagattggt ggacctcgct   1200
cttataccat cgcagttgct tccctgggta aaggagtggc ctgtaatcct gcctgcttca   1260
tcacacagct cctccctgtg aaaaggaagc tagggttcta tgaatggact tcaaggttaa   1320
gaagtcacat aaatcccaca ggcactgttt tgcttcagct agaaaataca atgcagatgt   1380
cattaaaaga cttactttaa aatgtttatt ttattgcc                            1418
```

<210> SEQ ID NO 4
<211> LENGTH: 20
<212> TYPE: PRT
<213> ORGANISM: Homo sapiens

<400> SEQUENCE: 4

Ile Val Tyr Ser Cys Glu Trp Pro Leu Tyr Met
                5                  10
Trp Pro Phe Gln Lys Pro Asn Tyr Thr
            15                  20

UNITED STATES PATENT AND TRADEMARK OFFICE
CERTIFICATE OF CORRECTION

| | |
|---|---|
| PATENT NO. | : 11,034,946 B2 |
| APPLICATION NO. | : 16/153371 |
| DATED | : June 15, 2021 |
| INVENTOR(S) | : David H. Calhoun et al. |

It is certified that error appears in the above-identified patent and that said Letters Patent is hereby corrected as shown below:

In the Claims

Claim 2, Column 21, Line 56:
Now reads: "g M208E"
Should read: -- M208 --

Signed and Sealed this
First Day of October, 2024

Katherine Kelly Vidal
*Director of the United States Patent and Trademark Office*